(12) United States Patent
Chmielewski

(10) Patent No.: US 10,932,070 B2
(45) Date of Patent: Feb. 23, 2021

(54) HEARING DEVICE WITH RECEIVER BACK-VOLUME AND PRESSURE EQUALIZATION

(71) Applicant: GN HEARING A/S, Ballerup (DK)

(72) Inventor: Anthony Chmielewski, Ballerup (DK)

(73) Assignee: GN Hearing A/S, Ballerup (DK)

( * ) Notice: Subject to any disclaimer, the term of this patent is extended or adjusted under 35 U.S.C. 154(b) by 0 days.

(21) Appl. No.: 16/450,609

(22) Filed: Jun. 24, 2019

(65) Prior Publication Data
US 2020/0404437 A1 Dec. 24, 2020

(51) Int. Cl.
*H04R 25/00* (2006.01)
*A61F 11/08* (2006.01)

(52) U.S. Cl.
CPC .............. *H04R 25/65* (2013.01); *A61F 11/08* (2013.01); *H04R 25/554* (2013.01); *H04R 25/60* (2013.01); *H04R 2460/11* (2013.01)

(58) Field of Classification Search
CPC .......... A61F 11/08; H04R 25/60; H04R 25/65; H04R 25/554; H04R 2460/11
See application file for complete search history.

(56) References Cited

U.S. PATENT DOCUMENTS

| | | | | |
|---|---|---|---|---|
| 6,728,385 | B2* | 4/2004 | Kvaløy | H04R 1/1016 381/317 |
| 8,878,735 | B2* | 11/2014 | Kvist | H01Q 13/10 343/718 |
| 10,687,153 | B2* | 6/2020 | Albahri | H04R 25/407 |
| 2014/0224283 | A1* | 8/2014 | Smith | H04R 25/654 134/37 |
| 2019/0116436 | A1* | 4/2019 | Lawand | H04R 1/1016 |
| 2019/0208343 | A1* | 7/2019 | Monti | H04R 25/652 |

* cited by examiner

*Primary Examiner* — Brian Ensey
(74) *Attorney, Agent, or Firm* — Vista IP Law Group, LLP

(57) ABSTRACT

A hearing device includes: a sound tube; a receiver configured to provide sound via the sound tube; a housing configured to accommodate the receiver; a compartment in the housing; and a channel extending from the compartment and terminating at a location that is in fluid communication with a space in the sound tube.

18 Claims, 6 Drawing Sheets

HEARING DEVICE WITH RECEIVER BACK-VOLUME AND PRESSURE EQUALIZATION

FIELD

This application relates generally to hearing devices, such as hearing protection devices, earbuds, earplugs, earphones, hearing aids, etc.

BACKGROUND

Hearing devices, such as hearing protection devices are used in many applications. For example, soldiers, fire fighters, rangers, rescuers, oil field operators, etc., sometimes may need to wear hearing protection devices in order to protect their hearing and/or to allow them to receive audio signals. Also, in certain types of missions or tasks, a person wearing a hearing protection device may experience a change of altitude or temperature. This creates a change in pressure in the ear canal, and may cause discomfort for the user. In some cases, the change in pressure may also interfere with an operation of the hearing protection device, such as a receiver (e.g., speaker) of the hearing protection device.

SUMMARY

Embodiments described herein relate to a hearing device which has a receiver back-volume for improving an acoustic bandwidth, and a pressure relief mechanism for relieving pressure from the receiver back-volume into an ear canal. The pressure may be due to altitude change or temperature change experienced by a user of the hearing device. The pressure may also be due to insertion of the hearing device into an ear canal.

A hearing device includes: a sound tube; a receiver configured to provide sound via the sound tube; a housing configured to accommodate the receiver; a compartment in the housing; and a channel extending from the compartment and terminating at a location that is in fluid communication with a space in the sound tube.

Optionally, the compartment defines a receiver back-volume configured to increase a sound bandwidth for the hearing device.

Optionally, the channel is configured to equalize pressure between the compartment and the space in the sound tube.

Optionally, the receiver comprises a first chamber, a second chamber, and a membrane between the first chamber and the second chamber; wherein the first chamber is associated with the sound tube; and wherein the second chamber is associated with the compartment.

Optionally, the channel is configured to equalize pressure between a first space outside the first chamber and a second space outside the second chamber.

Optionally, the hearing device further includes a receiver suspension, wherein at least a part of the channel is defined or covered by a portion of the receiver suspension.

Optionally, at least a part of the channel is between a wall of the compartment and a surface of the receiver.

Optionally, at least a part of the channel is defined by a wall of the compartment and/or a surface of the receiver.

Optionally, the compartment is sealed from a surrounding of a user of the hearing device when the hearing device is worn by the user.

Optionally, the channel is configured to relieve pressure in the compartment to the sound tube and/or vice versa.

Optionally, the hearing device further includes a microphone configured to provide a microphone signal, wherein the microphone is coupled to the receiver.

Optionally, the hearing device further includes an antenna configured to receive wireless signal, wherein the receiver is configured to provide the sound based on the wireless signal.

Optionally, at least a part of the channel is in the sound tube.

Optionally, the sound tube comprises an interior wall, and an opening at the interior wall; and wherein the opening at the interior wall of the sound tube is in fluid communication with the channel.

Optionally, the hearing device further includes a seal surrounding the sound tube.

Optionally, the hearing device is a hearing aid.

Optionally, the hearing device is a hearing protection device.

Optionally, the hearing device further includes a processing unit configured to perform signal processing based on a hearing loss characteristic of a user of the hearing device.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
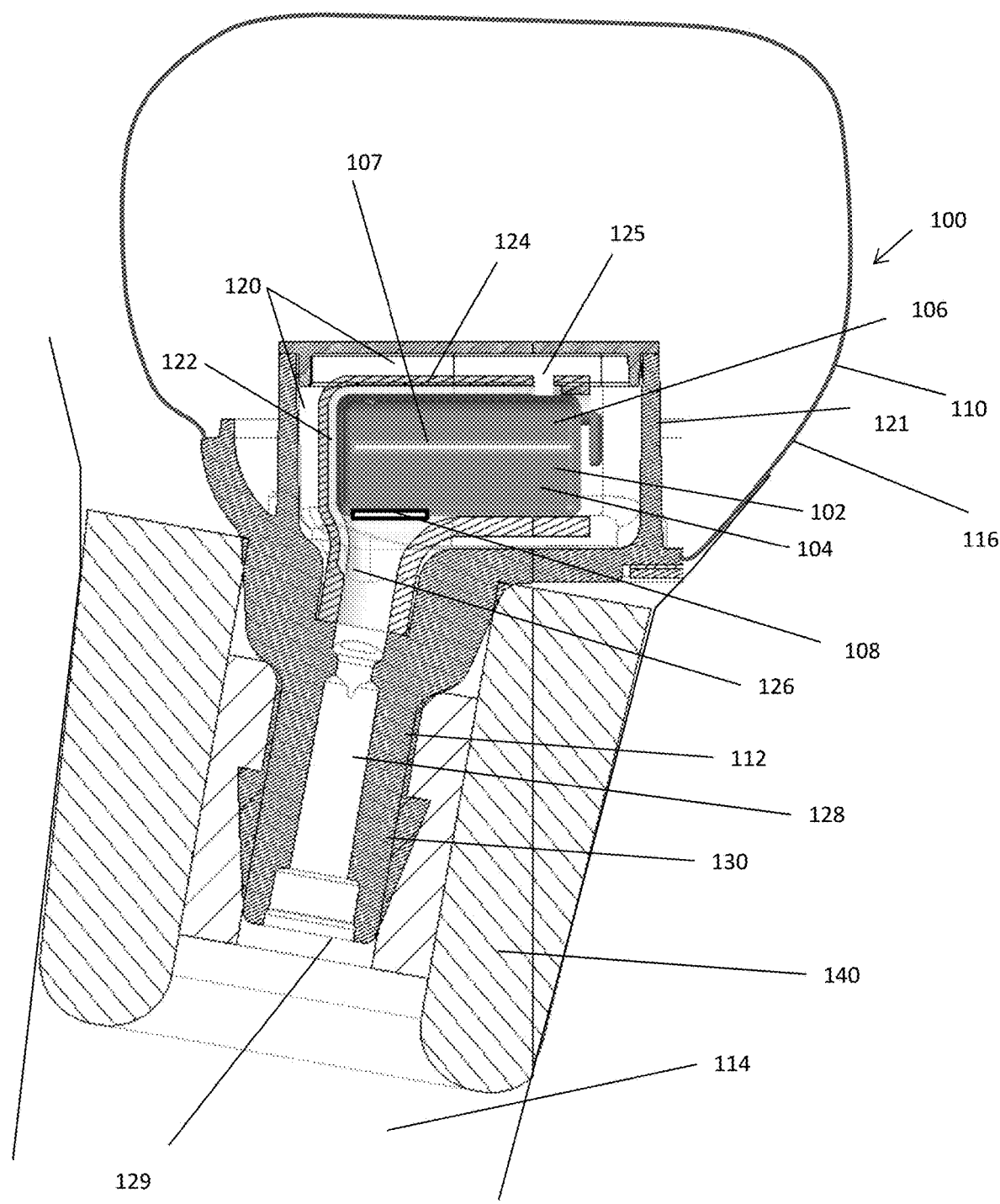
FIG. 1 illustrates a hearing device according to some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a hearing device 100. The hearing device 100 includes a receiver 102 configured to provide sound, and a housing 110. The housing 110 has a first portion 112 configured for placement in an ear canal 114, and a second portion 116 for containing the receiver 102. The hearing device 100 also includes a compartment 120 in the housing 110, and a channel 122 extending from the compartment 120 and terminating at a location that is in fluid communication with the ear canal 114 when the first portion 112 of the housing 110 is in the ear canal 114.

The compartment 120 defines a receiver back-volume configured to increase a sound bandwidth for the hearing device 100. As shown in the figure, the compartment 120 is at least partly surrounded by one or more compartment walls 121. The compartment 120 may surround the receiver 102 and/or receiver suspension 124. In the illustrated embodiments, the hearing device 100 includes a port 125 (e.g., a small pinhole) connected to the receiver back-volume. The receiver back-volume and the port 125 allow the receiver back-volume to operate like a subwoofer. In the illustrated embodiments, the port 125 is for connecting the channel 122 to the back-volume, and/or is for connecting the back-volume to the receiver 102 for providing subwoofer effect. In other embodiments, the hearing device 100 may have a first port for connecting the receiver 102 to the receiver back-volume of the compartment 120, and a second port for connecting the channel 122 to the receiver back-volume of the compartment 120. The first port may be a port (e.g. a small pinhole) in the receiver 102 (e.g. the housing of the receiver) and/or the second port may be a port (e.g. a small pinhole) in the receiver suspension 124. The first port may be placed near the second port. The first port and the second port may face each other and/or be placed with a distance from each other corresponding to the width of the channel 122.

The receiver back-volume provided by the compartment 120 is advantageous because it allows the receiver 102 to provide both good low frequency representation (e.g., lower than 200 Hz, lower than 150 Hz, lower than 100 Hz, lower than 50 Hz, etc.), as well as high frequency representation (e.g., up to at least 10 kHz or higher). This feature is advantageous over a solution in which two receiver parts are provided. In such cases, one receiver part takes care of high frequency, and the other receiver part takes care of low frequency, in order to achieve broader bandwidth. However, such solution takes up a lot of space. The compartment 120 providing the receiver back-volume allows the hearing device 100 to be made much smaller while providing desirable sound bandwidth. The receiver back-volume provided by the compartment 120 is also advantageous over another solution that involves use of a bigger receiver in order to achieve a desirable sound bandwidth, because the bigger receiver also takes up a lot of room as well. Thus, the receiver back-volume allows the hearing device 100 to provide desirable sound quality, and to be made smaller.

In the illustrated embodiments, the compartment 120 is sealed from an outside surrounding of a user of the hearing device 100 when the hearing device 100 is worn by the user. This feature allows the hearing device 100 to provide hearing protection for the user.

In the illustrated embodiments, the first portion 112 of the housing 110 comprises a sound tube 130. The channel 122 is configured to equalize pressure between the compartment 120 and a space in the sound tube 130. For example, pressure increase in the compartment 120 due to change in elevation or temperature may be relieved via the channel 122 into the ear canal 114. Also, pressure increase in the ear canal 114 may be relieved via the channel 122 into the receiver back-volume of the compartment 120.

Figure 2:
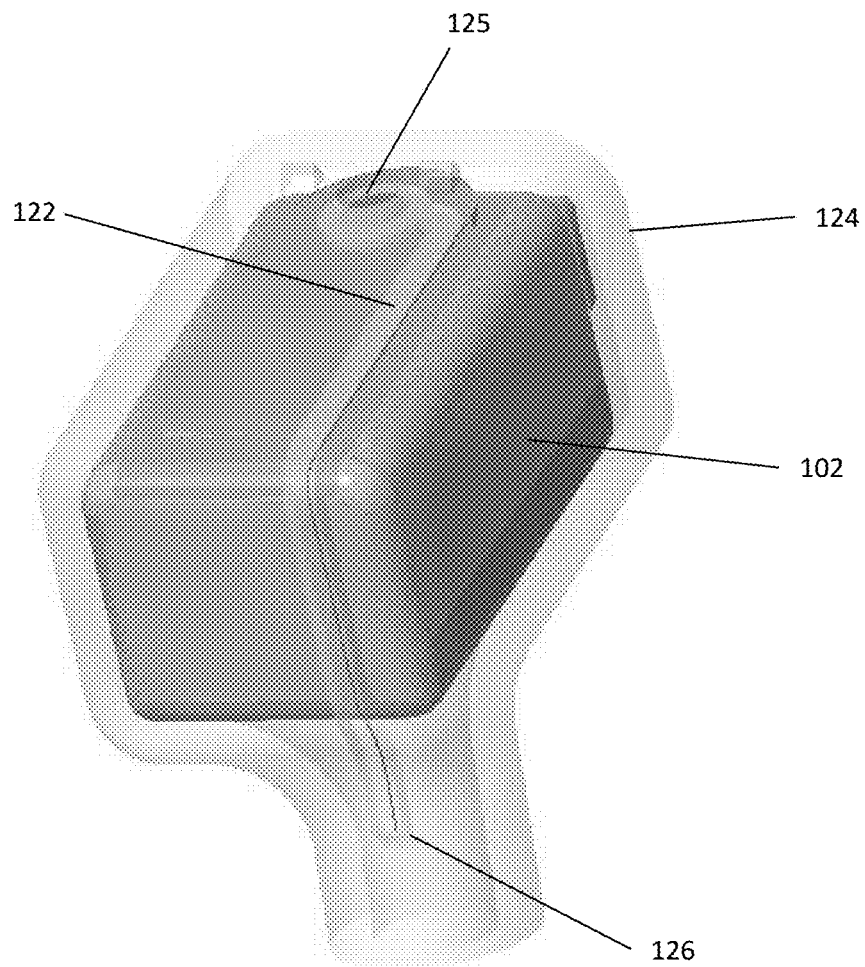
FIG. 2 illustrates a component of the hearing device of FIG. 1.

As shown in FIGS. 1-2, the hearing device 100 also includes a receiver suspension 124 configured to protect the receiver 102. In the illustrated example, the receiver 102 is contained in the receiver suspension 124, which at least partially mechanically decouples the receiver 102 from its surrounding. The receiver suspension 124 is advantageous because it protects the receiver 102 from being damaged in the event that the hearing device 100 is dropped on the ground, for example. The receiver suspension 124 is also advantageous because it reduces or eliminates feedback attributable from vibrations of the receiver 102. In one implementation, the receiver suspension 124 may include walls that are spaced apart from the receiver 102. The receiver 102 may be coupled to the receiver suspension 124 via one or more damping elements (e.g., damping springs, foam, etc.). In another implementation, the receiver suspension 124 may be made from a material that is more flexible than that of the housing 110, which allows the receiver 102 to move relative to the housing 110 if the hearing device 100 falls on the ground, hits another object, or undergoes extreme motion/acceleration. The receiver 102 may be directly coupled to the wall(s) of the receiver suspension 124, or indirectly coupled to the wall(s) of the receiver suspension 124 via another component, such as a spring, a connector, or a dampening element.

In some cases, the receiver suspension 124 may be considered to be a housing of the receiver 102. In other cases, the receiver suspension 124 may be considered to be a separate component that is configured to house the receiver 102 and the receiver housing. In further cases, the receiver suspension 124 may be considered to be components of the housing 110 of the hearing device 100. In further cases, the receiver suspension 124 with the receiver 102 may be considered to be one hardware component of the hearing device 100.

In other embodiments, the receiver suspension 124 is not required, and the hearing device 100 may not include the receiver suspension 124.

As shown in FIG. 1, the receiver 102 includes a first chamber 104 and a second chamber 106, separated by a membrane 107. The first chamber 104 is a front chamber, and the second chamber 106 is a back chamber. During use, a main part of sound from the receiver 102 is emitted through an opening 108 at the first chamber 104 into the sound tube 130. Some sound exits the receiver 102 through a small opening 125 (e.g., a pin hole) at the second chamber 106 into the receiver back-volume to provide a subwoofer effect (e.g., by amplifying sound in the low frequencies).

In some embodiments, at least a part of the channel 122 is between a wall of the receiver suspension 124 and a surface of the receiver 102. For example, as shown in FIG. 1, at least a part of the channel 122 is defined by the wall of the receiver suspension 124 and/or a surface of the receiver 102. In other embodiments, the channel 122 may be defined by a groove in a wall of the receiver suspension 124 and a surface of the receiver 102. In some cases, the channel 122 may be surrounded by a tube located between a wall of the receiver suspension 124 and the surface of the receiver 102.

In the illustrated embodiments, the channel 122 terminates at one end at an opening 126 that is in fluid communication with an output sound channel 128 of the hearing device 100, wherein the sound channel 128 terminates at a sound port 129. Therefore, the opening 126 of the channel 122 is also in fluid communication with the sound port 129, and in fluid communication with the ear canal 114 when the hearing device 100 is worn by a user. In the example shown in the figure, the opening 126 at which the channel 122 terminates is located at a wall that at least partially defines the output sound channel 128 of the hearing device 100. The wall may be an extension of the wall of the compartment 120, an extension of a wall of the receiver suspension 124, and/or an extension of a wall of the sound tube 130. In other embodiments, the channel 122 may extend further towards the distal end of the sound tube 130, and the opening 126 may be at an interior surface of a wall of the sound tube 130. In the illustrated embodiments, the channel 122 terminates at a second end at or in the vicinity of the port 125, or the first and/or second port. Accordingly, the second end of the channel 122 is in in fluid communication with the second chamber 106 of the receiver 102 and/or the compartment 120 defining the back-volume for the receiver 102.

As shown in FIG. 1, the hearing device 100 further includes a seal 140 surrounding the sound tube 130. The seal 140 is elastically deformable so that it can be compressed when placed in the ear canal 114 to thereby form a seal with the ear canal 114. The seal 140 may be made from a foam material (e.g., memory foam), polymer, plastic, or other materials that are capable of forming a seal with the ear canal 114. The seal 140 may allow the hearing device 100 to provide hearing protection for the user. The seal 140 may provide an airtight seal when inserted in the ear canal 114 of the user. In some embodiments, the seal 140 may provide a sound reductive seal from surrounding sounds when inserted in the ear canal 114 of the user.

During use of the hearing device 100, pressure within the compartment 120 defining the back-volume for the receiver 102, or pressure within the ear canal 114, may increase or decrease due to change of altitude or temperature or insertion of the hearing device 100 in the ear, etc. This may cause a pressure difference between the compartment 120 and the ear canal 114. Also, pressure difference (due to change of altitude, change of temperature, or insertion of the hearing device 100 in the ear, etc.) may exist between the first chamber 104 and the second chamber 106 of the receiver 102. The channel 122 is advantageous because it provides venting for the back-volume or the ear canal 114. For example, the channel 122 may relieve pressure in the compartment 120 into the ear canal 114. This is possible because the ear canal 114 has a volume that is larger than a volume of the back-volume of the compartment 120. As a result of the pressure relief mechanism provided by the channel 122 for relieving pressure from the receiver back-volume into an ear canal 114, the pressure in the compartment 120 may be equalized with the pressure in the ear canal 114. In other embodiments, the relief of the pressure may be in a direction that is opposite to that described—i.e., from the ear canal 114 to the receiver back-volume, if the pressure in the ear canal 114 is larger than that in the receiver back-volume. As shown in FIG. 1, by providing the channel 122 that extends between the space in fluid communication with the second chamber 106 and the space in fluid communication with the first chamber 104, the two pressures associated with the first and second chambers 104, 106 may be equalized via the channel 122. Accordingly, the channel 122 functions to (1) vent the second (back) chamber 106 of the receiver 102 and the receiver back-volume, (2) equalize pressure on each side of the membrane 107 in the receiver 102, and (3) prevent rupture of the membrane 107 due to a rapid and significant pressure difference between the first and second chambers 104, 106 of the receiver 102.

As illustrated in the above embodiments, the channel 122 is advantageous because it vents the receiver back-volume of the compartment 120 to inside the ear canal 114 instead of to the outside environment of the user. Venting the receiver back-volume to the outside environment does not allow the hearing device 100 to provide hearing protection because noise from the environment is not shielded due to such venting.

In some embodiments, the channel 122 may be made sufficiently narrow so that it does not interfere with, or has minimum interference on, the subwoofer effect provided by the receiver back-volume.

In some embodiments, the hearing device 100 with the above venting feature may be used in combat missions, in which a soldier may be required to undergo extreme change in altitudes and/or temperatures. For example, the soldier may be required to jump out of an airplane or helicopter, and to land after parachuting. In some cases, the soldier may go directly into water after jumping out of the airplane or helicopter, and may be submerged in water $2m$ down or deeper. The hearing device 100 described herein allows the soldier to be ready at different phases of the mission. In particular, when the soldier is wearing the hearing device 100 in the airplane, the hearing device 100 may protect the soldier from the noise of the airplane and/or may allow the soldier to hear radio signals. In some cases, radio signals may be used by the hearing device 100 for facilitating a call or a communication from another device (e.g., a base station, a cell phone, a radio, a communication device of a teammate, etc.). After the soldier jumps out of the airplane, the soldier may continue to receive radio signals via the hearing device 100. After the soldier lands, the solder may continue to wear the hearing device 100 for hearing protection. For example, the hearing device 100 may protect the soldier from loud noises, such as gun fire and bombing. Alternatively, if the soldier lands in water and submerges under the water, the hearing device 100 may provide a seal with respect to the ear canal, and may allow the soldier to continue receiving radio signals. In some cases, the soldier may at least be able to receive radio signals when being close to the surface. Accordingly, the hearing device 100 described herein is advantageous because it allows the soldier to be ready in different phases of a mission without the need to take off the hearing device 100. During any phase of a mission, if there is pressure difference between the first and second chambers 104, 106 on either side of the membrane 107, the venting feature will provide equalization of the pressure. In some embodiments, the hearing device 100 may have a small size, and may be made to be comfortable for worn, even over an extended period (e.g., up to 8 hours a day or longer).

In some embodiments, the hearing device 100 is configured to pass Environmental MIL-STD-810G Compliance requirements.

Also, in some embodiments, the hearing device 100 may be configured to be fully operable at all altitudes from at least the sea level to 40,000 ft.

Also, in some embodiments, the hearing device 100 may be configured to provide rapid compression or decompression, so that there e.g. will not be any rupturing of the hearing device or safety hazards due to rapid decompression from an equivalent altitude of 15,000 ft to an equivalent altitude of 40,000 ft within 15 seconds.

In some embodiments, the hearing device 100 is configured to meet the water immersion test under Test Method 512.5, Procedure I of MIL-STD-810G. During the test, test item is powered on, and is immersed in water to a level of 1 meter for not less than 30 minutes.

Figure 3A:
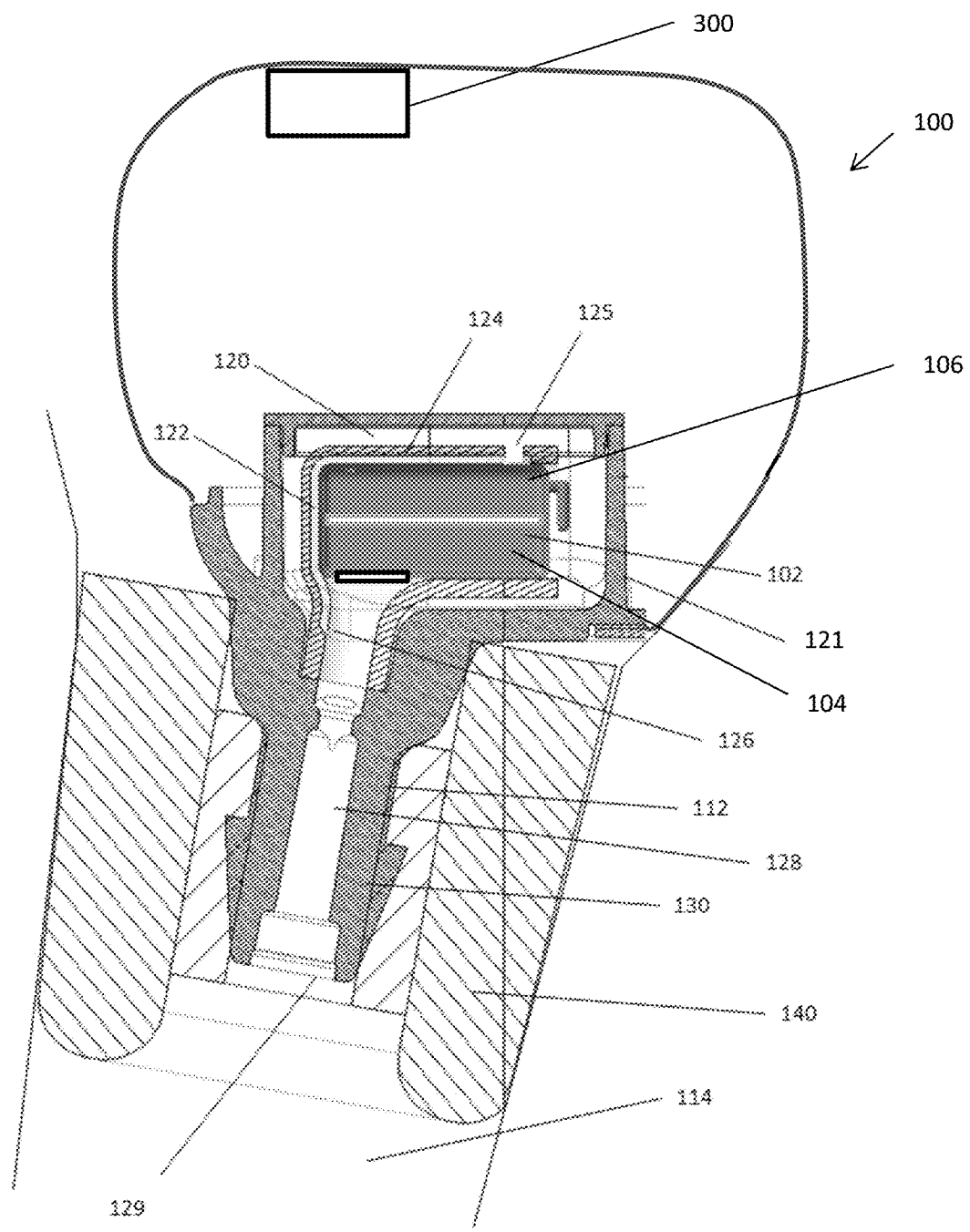
FIG. 3A illustrates a hearing device according to other embodiments.

In some embodiments, the hearing device 100 may optionally further include one or more microphones 300 configured to provide microphone signal(s), wherein the microphone(s) is coupled to the receiver 102 (FIG. 3A). In such cases, the housing 110 may include one or more microphone ports that are configured to receive sound. The microphone port(s) may be covered by a filter that blocks liquid while allowing sound to enter therethrough. During use, the microphone(s) 300 picks up sound around the user and generate corresponding microphone signal(s). The microphone signal(s) is transmitted to the receiver 102, which generates audio signal(s) (sound) for output into the ear canal. Having the microphone(s) 300 is advantageous because it allows the user of the hearing device 100 to hear real time audio information (e.g., voice from speaker) in the environment. In some cases, such feature may allow the user of the hearing device 100 to communicate with teammates, allies, or other persons not wearing any hearing device or communication device in a mission. In some embodiments, an output of the microphone 300 may be directly coupled to an input of the receiver 102. In other embodiments, the hearing device 100 may also include a processing unit. In such cases, an output of the microphone 300 may be coupled to an input of a processing unit in the hearing device 100, which processes microphone signals from the ear canal microphone 300. The processed microphone signals are then transmitted to the receiver 102, which converts the processed microphone signals into sound for output to an eardrum of the user of the hearing device 100.

In some embodiments, the hearing device 100 includes only one microphone 300. In other embodiments, the hearing device 100 may include multiple microphones 300. For example, the hearing device 100 may include two microphones 300 arranged in a front-an-back configuration. Such arrangement of microphones 300 allows the hearing device 100 to detect direction of sound. In some cases, the hearing device 100 may be configured to selectively operate in a first mode in which the microphones 300 operate as directional microphones, or in a second mode in which the microphones 300 operate as omnidirectional microphones.

Figure 3B:
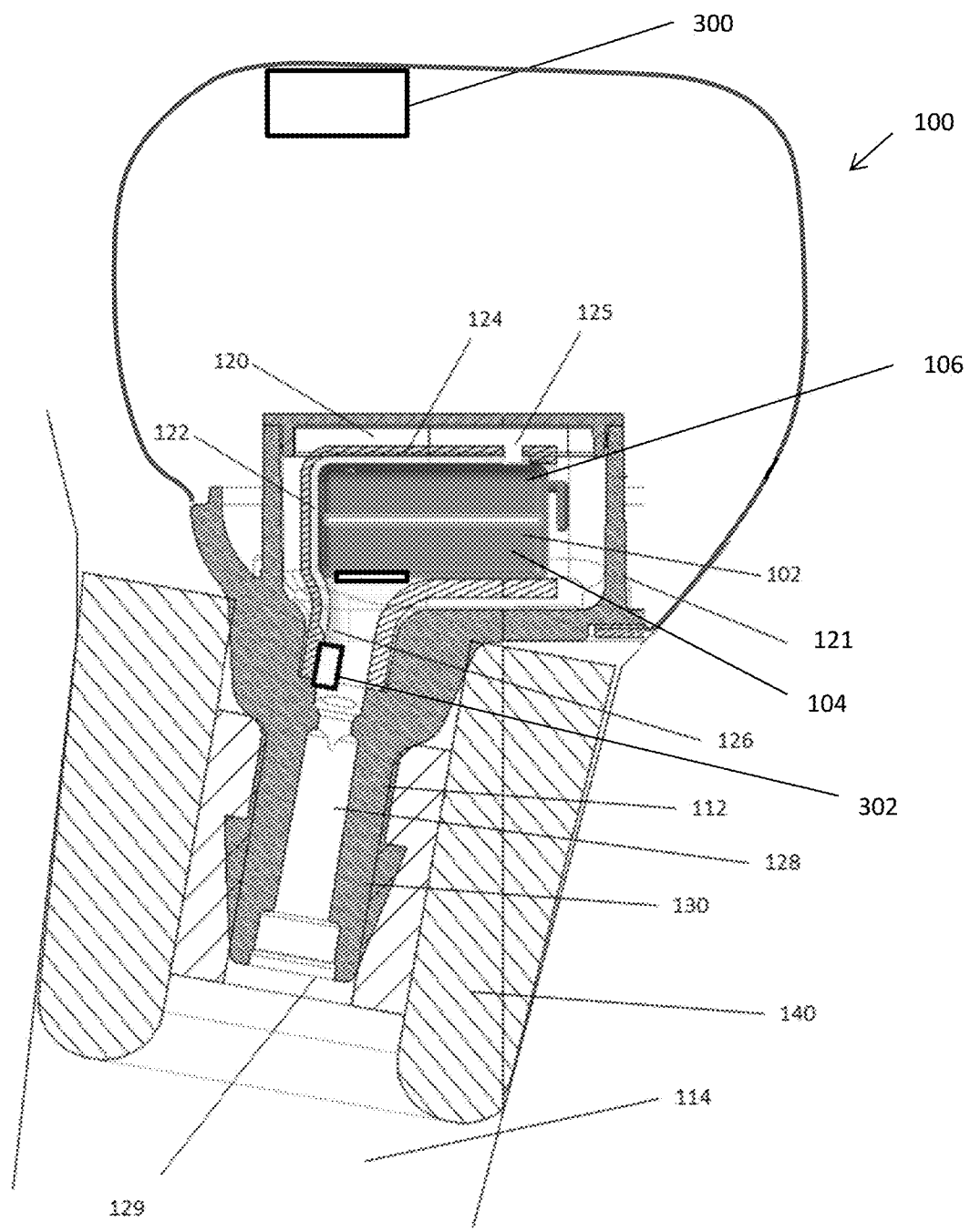
FIG. 3B illustrates a hearing device according to other embodiments.

In other embodiments, in addition to the microphone(s) 300 that is configured to pick up sound from the environment outside the user, the hearing device 100 may also include an ear canal microphone 302 configured to pick up sound from within the ear canal of the user (FIG. 3B). The ear canal microphone 302 is advantageous because it can pick up the user's own voice, and the picked-up voice may be processed by a processing unit of the hearing device 100 to provide feedback cancellation. In one implementation, an output of the ear canal microphone 302 may be coupled to an input of a processing unit, which processes microphone signals from the ear canal microphone 302 (e.g., reducing or eliminating feedback). The processed microphone signals are then transmitted to the receiver 102, which converts the processed microphone signals into sound for output to an eardrum of the user of the hearing device 100.

Figure 4:
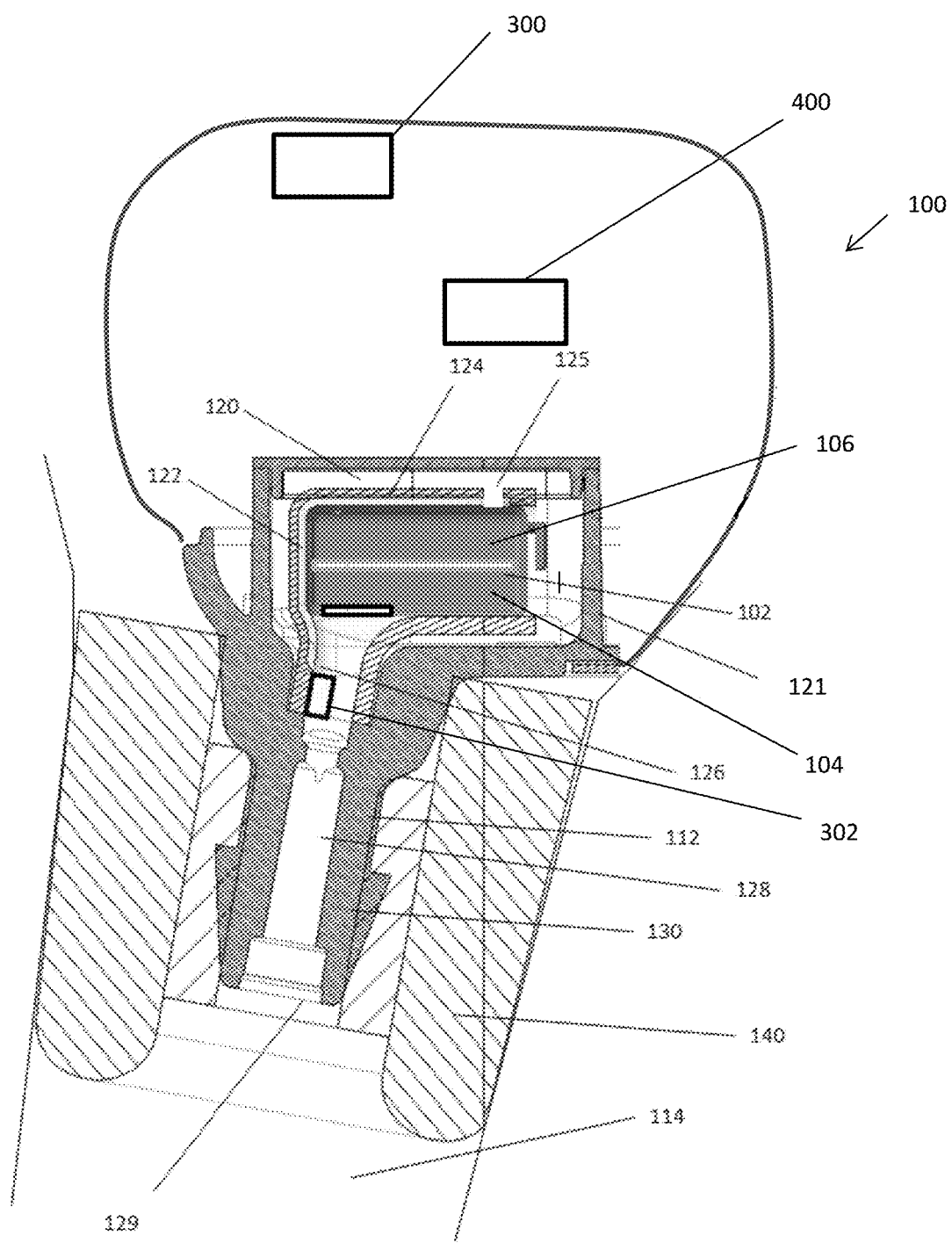
FIG. 4 illustrates a hearing device according to other embodiments.

As discussed, in some embodiments, the hearing device 100 may also include a processing unit configured to process microphone signals from microphone(s) 300 and/or microphone signals from ear canal microphone 302. FIG. 4 illustrates a hearing device 100 that includes a processing unit 400 configured to process microphone signal(s). The processing unit 400 is communicatively coupled between the microphone(s) 300 and the receiver 102, and is also communicatively coupled between the ear canal microphone 302 and the receiver 102. The processing unit 400 may be configured to process microphone signal(s) to provide noise cancellation, speech detection, speech enhancement, environment detection, or any combination of the foregoing.

The processing unit 400 may also include a sound enhancement module (not shown), such as a hearing loss processing module, configured to provide better hearing (e.g., provide hearing loss compensation). The sound enhancement module is configured to generate an enhanced sound signal (e.g., hearing loss compensated signal) based on the microphone signals provided by the microphone(s) 300 and/or the ear canal microphone 302. The receiver 102 then provides an acoustic signal based on the enhanced sound signal.

Figure 5:
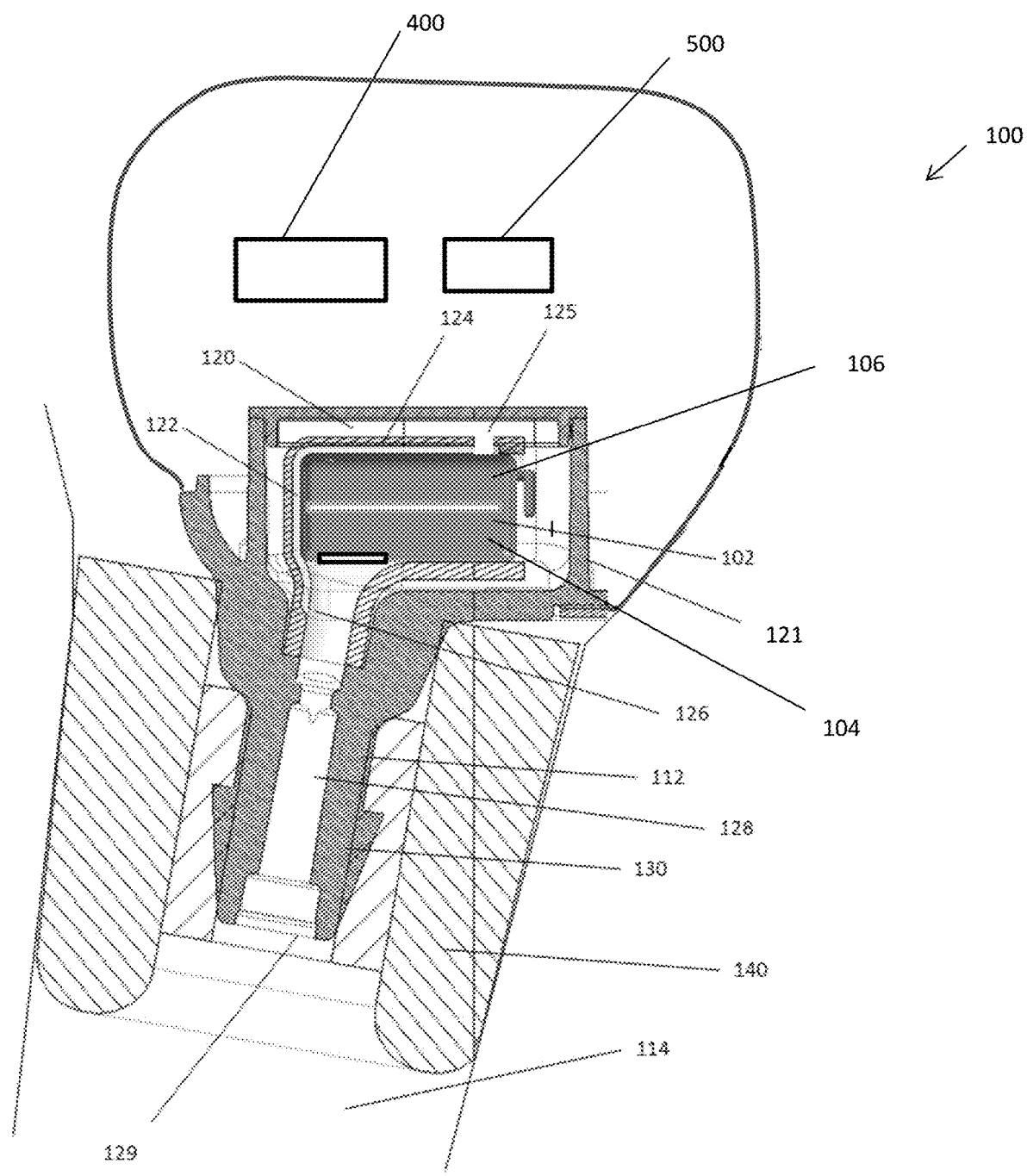
FIG. 5 illustrates a hearing device according to other embodiments.

Also, as shown in FIG. 5, in some embodiments, the hearing device 100 may further include an antenna 500 configured to receive wireless signal, wherein the receiver 102 is configured to provide the sound based on the wireless signal. In some cases, the antenna may receive wireless signal transmitted from another device (e.g., another hearing device, a communication device, a cell phone, a walkie-talkie, etc.) being used by another user. In other cases, the antenna may receive wireless signal transmitted from a base station (e.g., a radio station). The antenna is advantageous because it allows the hearing device 100 to receive radio messages. In further embodiments, the hearing device 100 may include a left hearing instrument and a right hearing instrument configured for worn by a user. In such cases, the left and right hearing instruments may be configured to communicate with each other via respective antennas in the hearing instruments.

In some embodiments, the hearing device 100 of FIG. 5 may also include the microphone(s) 300 and the ear canal microphone 302, as similarly discussed with reference to FIGS. 3-4. In such cases, the hearing device 100 may be configured to allow the user of the hearing device 100 to hear surrounding sounds, as well as real time radio messages (e.g., transmitted from a base station) and communication from teammates at the same time. The hearing device 100 may pick up sound from the teammates via the microphone(s) 300, or may receive communication from the teammates via an antenna if the teammates are communicating using communication devices (e.g., hearing devices).

It should be noted that the hearing device 100 should not be limited to have the size and shape illustrated in the example shown in FIG. 1. In other embodiments, the hearing device 100 may have other configurations (e.g., sizes and/or shapes, form factors, etc.).

In some embodiments, the hearing device 100 is a hearing protection device. In other embodiments, the hearing device 100 may be an earbud, an earplug, an earphone, or any of other types of hearing devices.

In further embodiments, the hearing device 100 may be a hearing aid. In such cases, the hearing device 100 further includes a processing unit configured to perform signal processing based on a hearing loss characteristic of a user of the hearing device 100. In some embodiments, the hearing device 100 configured as a hearing aid may also include filter(s), compressor(s), beamformer(s), or a combination of the foregoing. These components may be implemented as parts of the processing unit, or alternatively, be coupled to the processing unit.

In some embodiments, the hearing device 100 may be an in-the-ear (ITE) hearing aid. In other embodiments, the hearing device 100 may be other types of hearing aid. By means of non-limiting examples, the hearing device 100 may be an in-the-canal (ITC) hearing aid, a behind-the-ear (BTE) hearing aid with a BTE unit, or a receiver-in-the-ear (RITE) (also sometimes called a receiver-in-canal (RIC)) hearing aid. In some embodiments the hearing device 100 may be bilaterally fit (one hearing aid in each ear of the user). In such cases, the hearing device 100 may be a binaural hearing aid. Also, in some embodiments, the hearing device 100 may be an Over-The-Counter (OTC) hearing aid that may be obtained without a prescription. The OTC hearing aid may be an ITE hearing aid, an ITC hearing aid, a BTE hearing aid, a RIC hearing aid, or a binaural hearing aid.

In some embodiments, the hearing device 100 may optionally include a user interface (e.g., one or more button(s), one or more mechanical switch(es), one or more slider(s), one or more dial(s), etc., or any combination of the foregoing) for allowing a user to operate the hearing device 100. For example, such user interface may be configured to allow the user of the hearing device 100 to turn on or turn off the hearing device 100, adjust a volume of sound output by the receiver 102, accept a call or a communication from another device (e.g., a base station, a cell phone, a radio, a communication device of a teammate, etc.), change an operation mode of the hearing device 100, configure a functionality of the hearing device 100, etc.

In one or more embodiments described herein, the hearing device 100 may optionally further include a substrate, such as a printed circuit board (PCB) to which one or more components of the hearing device 100 may be coupled. Also, in some embodiments, the hearing device 100 may optionally further include one or more filters, one or more compressors, one or more beamformers, or any combination of the foregoing. The substrate, filter(s), compressor(s), and/or beamformer(s) may be accommodated inside the housing 110 of the hearing device 100.

It should be noted that the term "processing unit" may refer to software, hardware, or a combination of both. In some embodiments, the processing unit 400 may include one or more processor(s), and/or one or more integrated circuits.

Also, it should be noted that the term "microphone signal", as used in this specification, may refer to the signal directly outputted by a microphone, or it may refer to microphone signal that has been processed by one or more components (e.g., in a hearing aid). In addition, the term "microphone signal" may refer to one or more signal(s) output by a microphone, or output by a microphone and processed by component(s).

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

What is claimed:

1. A hearing device comprising:
   a sound tube;
   a receiver having a first side with a receiver opening, and a second side opposite from the first side, the receiver opening configured to output sound into the sound tube;
   a housing configured to accommodate the receiver;
   a compartment in the housing; and
   a channel extending from the compartment and terminating at a location that is in fluid communication with a space in the sound tube, wherein the location at which the channel terminates is away from the receiver opening, and is closer to the first side of the receiver with the receiver opening than to the second side of the receiver.

2. The hearing device of claim 1, wherein the compartment defines a receiver back-volume configured to increase a sound bandwidth for the hearing device.

3. The hearing device of claim 1, wherein the channel is configured to equalize pressure between the compartment and the space in the sound tube.

4. The hearing device of claim 1, wherein the receiver comprises a first chamber, a second chamber, and a membrane between the first chamber and the second chamber;
   wherein the first chamber is associated with the sound tube; and
   wherein the second chamber is associated with the compartment.

5. The hearing device of claim 1, wherein the channel is configured to equalize pressure between a first space outside the first chamber and a second space outside the second chamber.

6. The hearing device of claim 1, further comprising a receiver suspension, wherein at least a part of the channel is defined or covered by a portion of the receiver suspension.

7. The hearing device of claim 1, wherein at least a part of the channel is between a wall of the compartment and a surface of the receiver.

8. The hearing device of claim 1, wherein at least a part of the channel is defined by a wall of the compartment and/or a surface of the receiver.

9. The hearing device of claim 1, wherein the compartment is sealed from a surrounding of a user of the hearing device when the hearing device is worn by the user.

10. The hearing device of claim 1, wherein the channel is configured to relieve pressure in the compartment to the sound tube and/or vice versa.

11. The hearing device of claim 1, further comprising a microphone configured to provide a microphone signal, wherein the microphone is coupled to the receiver.

12. The hearing device of claim 1, further comprising an antenna configured to receive wireless signal, wherein the receiver is configured to provide the sound based on the wireless signal.

13. The hearing device of claim 1, wherein at least a part of the channel is in the sound tube.

14. The hearing device of claim 1, wherein the sound tube comprises an interior wall, and an opening at the interior wall; and
   wherein the opening at the interior wall of the sound tube is in fluid communication with the channel.

15. The hearing device of claim 1, further comprising a seal surrounding the sound tube.

16. The hearing device of claim 1, wherein the hearing device is a hearing aid.

17. The hearing device of claim 1, wherein the hearing device is a hearing protection device.

18. The hearing device of claim 1, further comprising a processing unit configured to perform signal processing based on a hearing loss characteristic of a user of the hearing device.

* * * * *